(12) United States Patent
Wood et al.

(10) Patent No.: US 9,539,334 B2
(45) Date of Patent: Jan. 10, 2017

(54) ORALLY DISSOLVING THIN FILMS CONTAINING ALLERGENS AND METHODS OF MAKING AND USE

(71) Applicant: THE JOHNS HOPKINS UNIVERSITY, Baltimore, MD (US)

(72) Inventors: Robert Wood, Lutherville, MD (US); Hai-Quan Mao, Baltimore, MD (US); Corinne Keet, Baltimore, MD (US); Russell Martin, Los Gatos, CA (US)

(73) Assignee: John Hopkins University, Baltimore, MD (US)

( * ) Notice: Subject to any disclaimer, the term of this patent is extended or adjusted under 35 U.S.C. 154(b) by 0 days.

(21) Appl. No.: 14/400,856

(22) PCT Filed: May 17, 2013

(86) PCT No.: PCT/US2013/041552
§ 371 (c)(1),
(2) Date: Nov. 13, 2014

(87) PCT Pub. No.: WO2013/173697
PCT Pub. Date: Nov. 21, 2013

(65) Prior Publication Data
US 2015/0125495 A1 May 7, 2015

Related U.S. Application Data

(60) Provisional application No. 61/648,106, filed on May 17, 2012.

(51) Int. Cl.
| | |
|---|---|
| A61K 39/35 | (2006.01) |
| A61K 47/38 | (2006.01) |
| A61K 45/06 | (2006.01) |
| A61K 47/10 | (2006.01) |
| A61K 9/00 | (2006.01) |
| A61K 9/70 | (2006.01) |
| A61K 47/26 | (2006.01) |
| B29C 39/02 | (2006.01) |
| A61K 47/32 | (2006.01) |
| B29L 7/00 | (2006.01) |

(52) U.S. Cl.
CPC ............... *A61K 47/38* (2013.01); *A61K 9/006* (2013.01); *A61K 9/7007* (2013.01); *A61K 9/7015* (2013.01); *A61K 39/35* (2013.01); *A61K 45/06* (2013.01); *A61K 47/10* (2013.01); *A61K 47/26* (2013.01); *B29C 39/02* (2013.01); *A61K 47/32* (2013.01); *B29L 2007/00* (2013.01)

(58) Field of Classification Search
CPC ........ A61K 47/38; A61K 39/35; A61K 47/32; A61K 9/006; A61K 9/7007
See application file for complete search history.

(56) References Cited

U.S. PATENT DOCUMENTS

| | | |
|---|---|---|
| 2002/0142042 A1 | 10/2002 | Mumper et al. |
| 2008/0044454 A1 | 2/2008 | Yang et al. |
| 2011/0142942 A1 * | 6/2011 | Schobel ................. A61K 9/006 424/489 |
| 2011/0243994 A1 | 10/2011 | Asari et al. |

FOREIGN PATENT DOCUMENTS

| | | |
|---|---|---|
| WO | 2004047794 A2 | 6/2004 |
| WO | 2010002418 A2 | 1/2010 |

* cited by examiner

*Primary Examiner* — Mina Haghighatian
(74) *Attorney, Agent, or Firm* — John Hopkins Technology Transfer (57) ABSTRACT

The present invention provides a thin mucoadhesive sublingual film composition which provides improved allergen delivery and efficacy at a smaller dose while prolonging the contact time between the allergen and oral antigen presenting cells (APCs), and therefore minimizing the risk of systemic side effects. The thin film compositions of the present invention are also easier to standardize, and removes any need for measuring allergen doses at the physician's office, and which allows for a simplified dosing schedule. Methods of making the thin film compositions and methods for their use are also disclosed.

7 Claims, 2 Drawing Sheets

ORALLY DISSOLVING THIN FILMS CONTAINING ALLERGENS AND METHODS OF MAKING AND USE

REFERENCE TO RELATED APPLICATIONS

This application is a 35 U.S.C. §371 U.S. national entry of International Application PCT/US2013/041552, having an international filing date of May 17, 2013, which claims the benefit of U.S. Provisional Patent Application 61/648, 106, filed on May 17, 2012, the content of each of the aforementioned applications is herein incorporated by reference in their entirety.

STATEMENT OF GOVERNMENTAL INTEREST

This invention was made with government support under grant no. RR025005 awarded by the National Institutes of Health. The government has certain rights in the invention.

BACKGROUND OF THE INVENTION

Peanut allergy affects about 1% percent of children in the United States, and the prevalence of this disease has increased dramatically in the past 20 years. Because peanuts and other food based allergies are pervasive, and reactions can occur to even minute quantities, these types of allergies pose substantial risks to individual health, and have significant negative impact on individual quality of life. Such allergies are typically life-long with a resolution rate of only about 20%. Avoidance of the allergens and treatment of accidental exposures have been the mainstays of therapy for allergic patients.

Allergen specific immunotherapy in the form of oral immunotherapy (OIT) and sublingual immunotherapy (SLIT) have recently shown some promise, however with these therapies, the composition is in liquid form and must be held under the tongue for a specified period of time and then swallowing, or orally, with the product mixed with food or drink and swallowed.

Current methods of therapy using aqueous drops are not optimized either for practicality or efficiency. Currently, the maximal sublingual dose has been limited by both the ability to generate stable concentrated extracts and by the amount of liquid that can tolerably be held under the tongue by a subject. In addition, the amount of time that the allergen extract remains in the mouth is practically limited.

As such, there still exists an unmet need for improved methods of immunotherapy to treat food and other types of allergies.

SUMMARY OF THE INVENTION

In accordance with an embodiment, the present invention provides a thin film pharmaceutical composition suitable for use in the treatment of an allergic response in a subject comprising a) about 10 to about 100% w/w of a primary film forming agent, wherein the agent comprises at least one or more water soluble polymers selected from the group consisting of pullulan, hydroxypropyl methyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, high amylase starch, hydroxypropylated high amylase starch, dextrin, pectin, chitin, chitosan, levan, elsinan, collagen, gelatin, zein, gluten, soy protein isolate, whey protein isolate, and casein, b) about 0.1 to about 20% w/w of a biodegradeable plasticizer selected from the group consisting of glycerols, sorbitol, poly(ethylene glycol), acetylated monoglycerides and alkyl citrates, c) about 0.1 to about 30% w/w of pharmaceutically acceptable excipients and carriers, d) about 0.1 to about 20% w/w of at least one or more mucoadhesive polymers, and e) 10 ng to about 50 mg or at least about 0.1% to about 50% w/w of at least one allergen extract.

In accordance with another embodiment, the present invention provides a method for preparing a quick-dissolving thin film composition comprising the pharmaceutical composition described above, the method comprising the steps of a) forming an emulsion of one or more allergen extracts, one or more primary film forming agents, one or more biodegradeable plasticizers, one or more pharmaceutically acceptable excipients and carriers, and one or more mucoadhesive polymers, b) dispersing the emulsion into a film forming solution, and c) forming a film from said dispersion.

In accordance with a further embodiment, the present invention provides a method for treatment of an allergic response to an antigen in a subject comprising administering to the subject a sufficient amount of at least one pharmaceutical composition described above.

DETAILED DESCRIPTION OF THE INVENTION

In accordance with one or more embodiments, the present invention provides a thin mucoadhesive sublingual film composition which addresses the practical concerns discussed above by allowing for allergen efficacy at a smaller dose while prolonging the contact time between the allergen and oral antigen presenting cells (APCs), and therefore minimizing the risk of systemic side effects. The thin film compositions of the present invention are also easier to standardize, and removes any need for measuring allergen doses at the physician's office, and which allows for a simplified dosing schedule.

In an embodiment, it will be understood that children, who will likely comprise a majority of the intended subjects, dosage administration is greatly facilitated due to the fact that children often cannot hold drops under the tongue for any prolonged length of time without swallowing. The mucoadhesive films of the present invention do not have the same swallowing restrictions. The thin film formulation preserves the allergen bioactivity and shows longer term stability compared to other pharmaceutical formulations. The film fabrication process is based in part, on the thin film compositions disclosed in WO 2010/002418, and incorporated by reference herein it its entirety.

As will be disclosed in more detail, the manufacture and use of the thin film compositions of the present invention are versatile, and can easily be extended to other allergens.

In accordance with an embodiment, the present invention provides a pharmaceutical composition suitable for use in the treatment of an allergic response in a subject comprising: a) about 10 to about 100% w/w of a primary film forming agent, wherein the agent comprises at least one or more water soluble polymers selected from the group consisting of pullulan, hydroxypropyl methyl cellulose, polyvinyl pyrrolidone, carboxymethyl cellulose, polyvinyl alcohol, sodium alginate, polyethylene glycol, xanthan gum, tragacanth gum, guar gum, acacia gum, arabic gum, polyacrylic acid, methylmethacrylate copolymer, carboxyvinyl polymer, high amylase starch, hydroxypropylated high amylase starch, dextrin, pectin, chitin, chitosan, levan, elsinan, collagen, gelatin, zein, gluten, soy protein isolate, whey protein isolate, and casein; b) about 0.1 to about 20% w/w of a biodegradable plasticizer selected from the group consisting of glycerols, sorbitol, poly(ethylene glycol), acetylated monoglycerides and alkyl citrates; c) about 0.1 to about 30% w/w of pharmaceutically acceptable excipients and carriers; d) about 0.1 to about 20% w/w of at least one or more mucoadhesive polymers; and e) 10 ng to about 50 mg or at least about 0.0001% to about 70% w/w of at least one allergen extract. In certain embodiments, the subject compositions of the present invention comprise about 1% to about 75% or more by weight of the total composition, alternatively about 2.5%, 5%, 10%, 20%, 30%, 40%, 50%, 60% or 70%, of at least one allergen extract.

It will be understood by those of ordinary skill in the art that the term "film-forming agents" as used in the cosmetic and pharmaceutical fields, typically includes hydrophilic polymers such as polyvinylpyrrolidone (PVP), acrylates, acrylamides, and copolymers thereof.

As used herein, the term "biodegradable plasticizers" are compounds that increase the fluidity or flexibility of the thin film and include poly-L-lactic acid, glycerols, sorbitol, poly (ethylene glycol), acetylated monoglycerides and alkyl citrates.

The precise effective amount for a human subject will depend upon the severity of the subject's disease state, general health, age, weight, gender, diet, time and frequency of administration, drug combination(s), reaction sensitivities, and tolerance or response to therapy. A routine experimentation can determine this amount and is within the judgment of the medical professional. Compositions may be administered individually to a patient, or they may be administered in combination with other drugs, hormones, agents, and the like.

With respect to the compositions described herein, the carrier can be any of those conventionally used, and is limited only by physico-chemical considerations, such as solubility and lack of reactivity with the active compound(s), and by the route of administration. The carriers described herein, for example, vehicles, adjuvants, excipients, and diluents, are well-known to those skilled in the art and are readily available to the public. It is preferred that the carrier be one which is chemically inert to the active agent(s), and one which has little or no detrimental side effects or toxicity under the conditions of use. Examples of the carriers include soluble carriers such as known buffers, which can be physiologically acceptable (e.g., phosphate buffer) as well as solid compositions such as solid-state carriers or latex beads.

The carriers or diluents used herein may be solid carriers or diluents for solid formulations, or mixtures thereof.

Solid carriers or diluents include, but are not limited to, gums, starches (e.g., corn starch, pregelatinized starch), sugars (e.g., lactose, mannitol, sucrose, dextrose), cellulosic materials (e.g., microcrystalline cellulose), acrylates (e.g., polymethylacrylate), calcium carbonate, magnesium oxide, talc, or mixtures thereof.

Further carriers or excipients include binders (e.g., acacia, cornstarch, gelatin, carbomer, ethyl cellulose, guar gum, hydroxypropyl cellulose, hydroxypropyl methyl cellulose, povidone), buffers (e.g., Tris-HCl., acetate, phosphate) of various pH and ionic strength, additives such as albumin or gelatin to prevent absorption to surfaces, solubilizing agents (e.g., cremophor, glycerol, polyethylene glycol, benzlkonium chloride, benzyl benzoate, cyclodextrins, sorbitan esters, stearic acids), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., aspartame, citric acid), preservatives (e.g., thimerosal, benzyl alcohol, parabens), emulsifiers (e.g., carbomer, hydroxypropyl cellulose, sodium lauryl sulfate), and/or adjuvants.

In accordance with an embodiment, the present invention provides a pharmaceutical composition as described above, further comprising: f) about 0.01 to about 0.1% w/w of a coloring agent; and g) about 0.1 to about 10% w/w of a flavoring agent.

Flavoring agents among those useful herein include any material or mixture of materials operable to enhance the taste of the present composition. Any orally acceptable natural or synthetic flavorant can be used, such as flavoring oils, flavoring aldehydes, esters, alcohols, similar materials, and combinations thereof. Flavoring agents include vanillin, sage, marjoram, parsley oil, spearmint oil, cinnamon oil, oil of wintergreen (methyl salicylate), peppermint oil, clove oil, bay oil, anise oil, *eucalyptus* oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, *eucalyptus* oil, eucalyptol, anethole, eugenol, *cassia*, oxanone, .alpha.-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), 1-menthol, carvone, anethole, eugenol, limonene, peppermint oil, spearmint oil, ocimene, n-amyl alcohol, citronellol, a-terpineol, methyl salicylate, methyl acetate, citronellol acetate, cineol, linalool, ethyl linalool, capsaicin and mixtures thereof. One or more flavorants are optionally present in a total amount of about 0.01% to about 5% by weight, optionally in various embodiments from about 0.05 to about 2% by weight, from about 0.1% to about 2.5% by weight, and from about 0.1 to about 0.5% by weight.

Colorants among those useful herein include pigments, dyes, lakes and agents imparting a particular luster or reflectivity to the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof. One or more colorants are optionally present in a total amount of about 0.001% to about 20% by weight, for example about 0.01% to about 10% by weight or about 0.1% to about 5% by weight.

Sweetening agents of the present invention include sodium saccharin, aspartame, sucralose, thaumatin, acesulfame potassium, stevioside, stevia extract, paramethoxy cinnamic aldehyde, neohesperidyl dihydrochalcone and perillartine. Sweeteners among those useful herein also include orally acceptable natural or artificial, nutritive or non-nutritive sweeteners. Such sweeteners in the present invention can include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from about 0.005% to about 5% by weight, optionally from about 0.01% to about 10% by weight.

In accordance with a further embodiment, the present invention provides a pharmaceutical composition as described above, wherein the composition is prepared as a thin film with a range of thickness. In an embodiment, the thickness of the thin films of the present invention can be between about 10 µm to about 1 mm, preferably between about 20 µm to about 800 µm, and more preferably between about 50 to about 500 µm.

In accordance with an embodiment, the present invention provides a pharmaceutical composition as described above, wherein the thin film is cut into strips. The shape of the strips can be any shape desired that can accommodate oral or buccal delivery or placement. The dimensions of the strips can be between 0.25×0.25 mm to about 2.0×2.0 cm. In an embodiment, the strips of the present invention have dimensions of about 1×2 cm. It will be understood by those of skill in the art that the films of the present invention can be shaped into any particular size or dimension depending on the dose and route of administration.

It will be understood by those of ordinary skill in the art that mucoadhesive polymers are used in the thin film compositions of the present invention. It is known that the use of a mucoadhesive polymer will attach to related tissue or to the surface coating of the tissue for the targeting various absorptive mucosa such as ocular, nasal, pulmonary, buccal, vaginal etc. There are two broad classes of mucoadhesive polymers: hydrophilic polymer and hydrogels. In the large classes of hydrophilic polymers those containing carboxylic group exhibit the best mucoadhesive properties, poly vinyl pyrrolidone (PVP), methyl cellulose (MC), sodium carboxymethylcellulose (SCMC), hydroxypropyl cellulose (HPC) and other cellulose derivatives. Hydrogels are the class of polymeric biomaterial that exhibit the basic characteristics of hydrogels to swell by absorbing water interacting by means of adhesion with the mucus that covers epithelia, and include cationic, anionic and neutral hydrogels (e.g., chitosan, carbopol, and Eudragit). All mucoadhesive polymers have certain specific characters like high molecular weight and viscosity, long chain length, and flexibility of chain. These polymers also include co-polymers such as a copolymer of PAA and PEG monoethylether monomethacrylate (PAA-co-PEG), for example.

In accordance with another embodiment, the present invention provides a pharmaceutical composition as described above, wherein the mucoadhesive polymers are naturally occurring and/or synthetic, and are selected from the group consisting of chitosan, hyaluronate, alginate, gelatin, collagen, poly(acrylic acid), poly(methacrylic acid), poly(L-lysine), poly(ethyleneimine), hydroxylpropyl methylcellulose, poly(ethylene oxide), poly(2-hydroxyethyl methacrylate), and derivatives or copolymers thereof.

As used herein, in an embodiment, the term "allergen extract" means an extract of allergenic components from a crude preparation of an allergen, such as weed, grass, or tree pollen, molds, house dust, or animal dander, used for diagnostic skin testing or for immunotherapy for allergy. In another embodiment, the proteins from the allergenic extract can be isolated and purified. Allergenic source materials include pollens, animal dander, fungal spores, house dust mite fecal particles, insect venoms, and foods. Allergen extracts are prepared by aqueous extraction of allergenic source materials obtained from natural sources. The production process is intended to be compatible with the physiological conditions to which the allergen is exposed upon contact with the human body. Allergens enter the body in various ways and encounter different physiologic conditions during the process. Food allergens must pass the acidic barrier of the stomach in order to reach the immunological centers in the intestine. Thus, food allergens must be resistant to the chemical and enzymatic degradation occurring in the stomach. An exception to this generalization are food allergens with structural similarities to pollen allergens, which can elicit symptoms in pollen-sensitized people while in contact with the oral mucosa. This type of reaction underlies oral allergy syndrome, a type of food allergic reaction.

In accordance with another embodiment, the present invention provides a pharmaceutical composition as described above, wherein the allergen extract is selected from the group consisting of peanut extract, tree nut extract, milk extract, shellfish extract, cockroach extract, cat hair extract, cat pelt extract, dust mite extract, grass extract, insect venom extract, dog hair extract, food extracts, meat extracts, urine extracts, such as mouse urine extract, for example, and egg extracts. In some embodiments, the allergen extract is a nut extract. In a preferred embodiment, the allergen extract is a peanut extract.

The extraction procedure should resemble the physiological conditions in the human body (i.e., pH 6 to 9 and ionic strength 0.05 to 0.2) and must avoid denaturing the proteins/allergens (i.e., organic solvents should be excluded). The process should be mild enough to avoid decomposition. Low-molecular-weight material (i.e., below 5000 Da), which is primarily composed of non-allergenic pigments and salts, may also contain pharmacologically active substances and may be removed. The processing procedure should include assessment of known toxins, viral particles, microorganisms, free histamines, etc, verifying their concentration below defined thresholds. Foods constitute a particularly diverse and difficult area, and the availability of standardized extracts is correspondingly limited. Foods are often derived from various cultivars and subspecies grown under a broad variety of conditions. Differences in tissue distribution and solubility properties of individual allergens may prevent optimal yields in a single extraction procedure. In such cases, a superior extract is derived by combining extracts produced using different buffers and different tissues (e.g., peel and pulp for fruits). Processing of the extract in an attempt to mimic digestion is specifically avoided, as some allergens causing oral allergy syndrome may be destroyed by such procedures. In addition, although some foods are typically cooked prior to ingestion, cooking unpredictably affects the allergenicity of the foods and so attempts are not made to recreate the effects of cooking in producing food extracts.

Allergen extracts are sometimes modified chemically or physically. The purpose of these modification steps is twofold: a) stabilization of the allergenic proteins in the extract; and b) attempts to balance efficacy with safety. The issue of efficacy versus safety is most important for specific immunotherapy. Administration of an allergen extract to which the patient is allergic will inevitably cause allergic adverse reactions with a small but significant frequency. Attempts to circumvent this problem include modification of the allergen extract either by chemical or physical means to enhance immunogenicity, although these modifications can also reduce allergenicity. The goal of this work is the creation of allergens that are more potent, i.e. capable of inducing the immunologic changes responsible for treatment benefit, but with less tendency to induce allergic adverse reactions.

Chemical modification. Allergen extracts for use in immunotherapy may be chemically modified using formaldehyde or glutaraldehyde. The chemical reaction results in intra- and intermolecular cross-linking, which yields high-molecular-weight complexes (i.e., allergoids). Although intended to reduce IgE binding while preserving immunogenicity, chemical modification, in practice, does not seem to increase safety. Without being limited to any particular theory, the likely explanation is that the chemical modification not only reduces allergenicity, but also immunogenicity, necessitating the use of higher doses.

Physical modification. Use of allergen extracts coupled to inorganic gels, such as aluminum hydroxide, increases the safety of immunotherapy through dual effects of the carrier. Coupling creates a depot effect, resulting in slow release of allergens to the tissue, and the gel provides an adjuvant effect, resulting in a more pronounced immune response to the vaccine. In Europe, most products for subcutaneous injection immunotherapy are aqueous extracts or allergoids absorbed to aluminum hydroxide.

As used herein the term "pharmaceutically active compound" or "therapeutically active compound" means a compound useful for the treatment or modulation of a disease or condition in a subject suffering therefrom. Examples of pharmaceutically active compounds can include any drugs known in the art for treatment of disease indications.

Other therapeutically active compounds included in the pharmaceutical compositions suitable for use in the thin film compositions of the present invention include antacids, antibiotics, antiemetic agents, antidepressants, and antifungal agents, anti-inflammatory agents, antiviral agents, anti-cancer agents, immunomodulatory agents, beta-interferons, hormones or cytokines.

In accordance with an embodiment, the present invention provides methods for preparing a quick-dissolving thin film composition comprising the pharmaceutical compositions described herein, the method comprising the steps of: a) forming an emulsion of one or more allergen extracts, one or more primary film forming agents, one or more biodegradeable plasticizers, one or more pharmaceutically acceptable excipients and carriers, and one or more mucoadhesive polymers; b) dispersing the emulsion into a film forming solution; and c) forming a film from said dispersion.

In accordance with another embodiment, the present invention provides methods for preparing a quick-dissolving thin film composition comprising the pharmaceutical compositions described herein, wherein the allergen extract is prepared as a solution comprising the steps of: a) suspending the extract powder at about a 20% w/v in deionized water to make an extract solution; b) incubating the extract solution at 37° C. for about 30 to 60 minutes; c) subjecting the extract solution to centrifugation at 3,000×g for 15 to 30 minutes; and d) collecting the supernatant of c).

In accordance with yet a further embodiment, the allergen extract used in the pharmaceutical compositions of the present invention is commercially prepared.

In accordance with still another embodiment, the present invention provides methods for preparing a quick-dissolving thin film composition comprising the pharmaceutical compositions described herein, wherein the forming of the film comprises: a) casting the film forming solution onto a non-stick surface; b) drying the film by exposing the solution to heat and/or a low humidity environment for between about 2 hours to about 48 hours, preferably between about 6 hours to about 40 hours, and more preferably between about 12 hours to about 36 hours; c) removing the dried film from the surface of a); and d) cutting the film to the desired size.

It will be understood by those of ordinary skill that drying the film can be performed by many methods known, including direct or indirect heating, infrared exposure, desiccation, etc. The time for drying is dependent on the particular pharmaceutical formulation and water content and is well within the skill of those in the art.

In accordance with an embodiment, the present invention provides methods for treatment of an allergic response to an antigen in a subject comprising administering to the subject a sufficient amount of at least one pharmaceutical composition as disclosed herein, wherein the route of administration is oral, buccal or sublingual. In a preferred embodiment, the route of administration is sublingual.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of allergy in a mammal. Furthermore, the treatment or prevention provided by the inventive method can include treatment or prevention of one or more conditions or symptoms of allergy being treated or prevented. Also, for purposes herein, "prevention" can encompass delaying the onset of the disease, or a symptom or condition thereof.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

An effective amount of the thin film composition of the present invention, to be employed therapeutically will depend, for example, upon the therapeutic and treatment objectives, the route of administration, the age, condition, and body mass of the subject undergoing treatment or therapy, and auxiliary or adjuvant therapies being provided to the subject. Accordingly, it will be necessary and routine for the practitioner to titer the dosage and modify the route of administration, as required, to obtain the optimal therapeutic effect. A typical daily dosage might range from about 0.1 ng to up to about 100 mg or more, preferably from about 100 ng to about 50 mg depending on the above-mentioned factors. Typically, the clinician will administer antibody until a dosage is reached that achieves the desired effect. The progress of this therapy is easily monitored by conventional assays.

In accordance with an embodiment, the present invention also provides a kit comprising at least one of the pharmaceutical compositions disclosed herein, in an airtight, opaque container, and instructions for use.

EXAMPLES

Based on earlier pilot studies, a solvent casting method is used to prepare the thin film strips to deliver a peanut extract. The main film polymer component is hydroxy propyl methylcellulose. Other polymers such as Eudragit (with low acrylic content), polyvinyl alcohol, polyethylene glycol and sodium alginate are added to modulate film dissolution time and allergen release time. Films with 10 mg of peanut allergen per film are used for this film release kinetic studies.

Thin strip formation. A film forming solution is prepared by dissolving hydroxypropyl methylcellulose (0-10 w/v %), Eudragit (0-10 w/v %, with low acrylic content), polyvinyl alcohol (0-10 w/v %), and sodium alginate (0-10 w/v %). Peanut extract powder is dissolved in the film forming solution together with stabilizing excipients such as sucrose, trehalose and glycerol. The resulting solution is then cast on a flat TEFLON mold, and dried in a chamber with convective airflow at between about 10° C. to about 60° C. for between 5 to 10 hours. The dried film is cut into strips of approximately 1 inch×1 inch.

Physical characterization of the films. The physical properties of the films of the present invention (uniformity, toughness, and wettability) dissolution time, and allergen release rate are all tested as follows. The mechanical strength and toughness of the films are tested on an Instron test machine (n=10). The dissolution time and total protein release are tested by submerging the thin film strips (n=10) into 0.5 ml of 10 mM PBS buffer (pH 7.4) at about 37° C. in a glass scintillation vial and maintained at the same temperature. An aliquot of 50 µl of supernatant is withdrawn at specific intervals and measured for absorbance at 280 nm.

Mucoadhesiveness, allergen release, and integrity of released allergens. Film strips with different protein doses are prepared to make sure that the overall protein release kinetics are maintained. This is achieved by using polyvinyl alcohol as a filler. For each of the following assays, each study is done on 10 samples at each dose level to determine the coefficient of variation between samples. A coefficient of variation of <10% is considered an adequate level of reproducibility.

Mucoadhesiveness. The mucoadhesive strength of the thin film strips is studied at room temperature using an INSTRON universal testing instrument using a method reported by Kim et al. (Arch. Pharm. Res., 2007; 30(3):381-6).

Release of Ara h1 and Ara h2 proteins. The supernatant samples from the release study are analyzed for the quantity of Ara h1 and Ara h2 proteins, respectively, through the use of monoclonal antibody based ELISA (Indoor Biotechnologies, Inc.).

Pilot clinical study. The pilot study includes 15 peanut allergic adults, who have both clinical and serologic evidence of peanut allergy. After enrollment, dosing will start at a dose of 0.1 µg. Biweekly escalations are done in the GCRC, with an initial goal of 10 mg over 20 weeks, with a two week maintenance period. Daily doses will be taken at home. The safety of office and home doses will be assessed. Biomarkers, including skin test reactivity, basophil histamine release, and serum IgE, IgG, and IgG4 is assessed at baseline and at completion of the study, but the primary outcome will be safety of this preparation. When the safety data are adequate, a larger controlled study of the efficacy and safety of the sublingual film is performed.

Example 1

Preparation of Mucoadhesive Thin Film Strips with Different Components

TABLE 1

| Film Component | F11 | F22 | F24 |
|---|---|---|---|
| Methocel E15 (% w/w of dry film) | 95.23 | 80.81 | 0.00 |
| Methocel F50 (% w/w of dry film) | 0.00 | 0.00 | 80.81 |
| Glycerol (% w/w of dry film) | 4.76 | 4.04 | 4.04 |
| Peanut Extract (% w/w of dry film) | 0.00992 | 15.15 | 15.15 |

The Formulation F11 film strip contains 2 micrograms of soluble peanut extract/strip. The Formulation F22 film strip contains 3 milligrams of soluble peanut extract/strip. The Formulation F24 film also contains 3 milligrams of soluble peanut extract/strip.

The films were prepared according to the following steps: 1) the allergen solution is prepared by suspending the peanut extract powder at 20% w/v in deionized water, then incubating the suspension at 37° C. for 30 minutes, followed by centrifuging the suspension at 3,000×g for 15 minutes, and collecting the supernatant; 2) Methocel E15, or F50, and glycerol, are mixed with the peanut extract solution according to the quantities listed above, with vortexing and ultrasonic vibration used to mix the solution until it is uniform and bubble-free; 3) the mixture solution is cast onto a flat surface or tray made of Teflon; 4) The film solution is dried by placing the cast film in an oven at 37° C. for 12 hours; 5) The dried filmstrips are removed from the tray and are cut to strips of dosing size, 1 cm×2 cm×200 µm each.

Example 2

Modulation of Allergen Release Time by Varying Polymer Weight

Three sets of thin film strips were prepared according to method described in Example 1 (F22) with 19.0 mg of HPMC with different molecular weights (viscosity number, 5 cP, 15 cP, and 50 cP, respectively), while all other film components held constant with 1 mg glycerol per strip and 3.6 mg of soluble peanut extract per strip.

Figure 1:
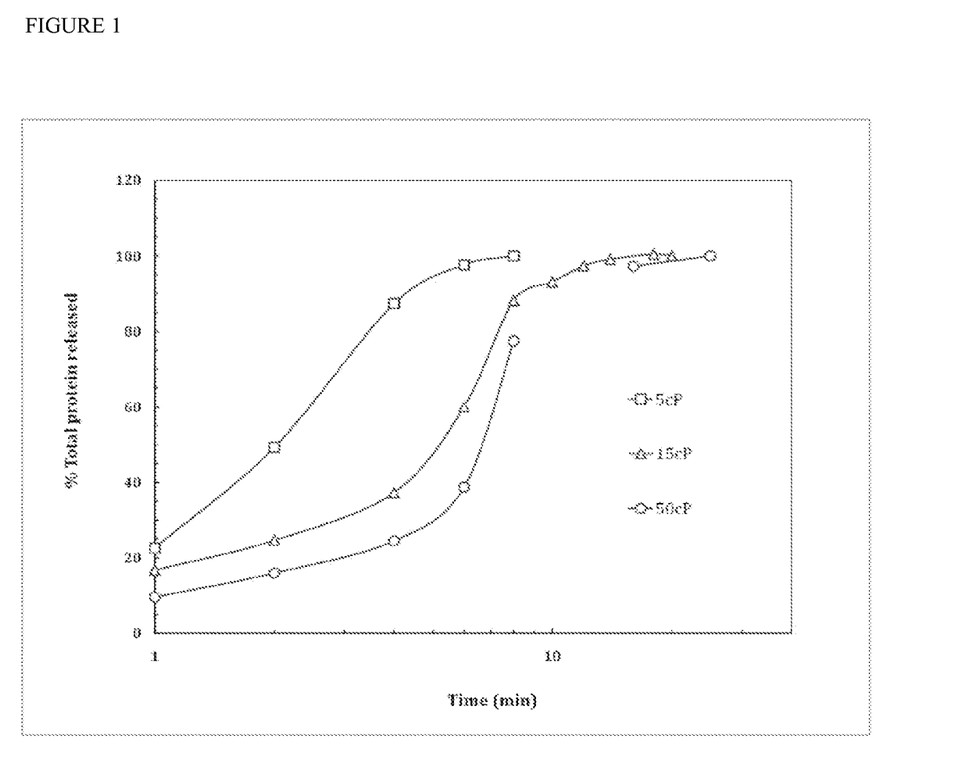
FIG. 1 is a graph depicting the effect of different concentrations of HPMC on the dissolution time of the thin film compositions of the present invention.

Dissolution time was measured by adding strips to 40 mL of phosphate-buffered saline (PBS) at 37° C. in a 50 mL Pyrex beaker. The solution was agitated by a 1 cm Teflon-coated stir bar rotating at 200 rpm. At different time points, 300 µl of samples were taken and measured on an UV/Vis spectrophotometer (Shimadzu UV mini 1240) at wavelengths of 214 nm, 230 nm, and 280 nm. The resulting absorbance values were correlated with those of a serially-diluted peanut protein standard. Results are shown in FIG. 1. The results showed that increasing the viscosity and thus the molecular weight of HPMC decreases the dissolution rate.

The total peanut extract release time ranged from 6 to 12 minutes for these three film strip samples.

Example 3

Sublingual Film Study

Twenty-five healthy volunteers were enrolled a study of dissolution time and preferred flavor of the sublingual films. The sublingual films contained either methocel 5 or methocel 15 in order to vary the dissolution time. Films containing methocel 5 took an average of 3.54±1.79 minutes to dissolve. While films containing methocel 15 took an average of 6.76±3.02 minutes to dissolve. Some participants also felt lingering flavor and residue in their mouths after the film dissolved, but neither of these sensations was unpleasant.

The most preferred film flavor was chocolate. Cream was the second most preferred flavor while grape and mixed berry were the least preferred. There were no adverse events or effects reported by study volunteers. Most participants found the film(s) pleasant tasting regardless of flavor. Only one volunteer rated a flavor (mixed berry) the lowest possible rating, a 5, and stated that she did not like the flavor at all.

Example 4

Preparation of Film Strips with High Loading Level of Allergen

This allergen loading method is designed to accommodate high allergen-loading levels. By implementing a concentration step for the allergen solution via tangential flow filtration, the maximum allergen loading can be raised to 2.4 mg of Ara h2, which is equivalent to a total protein loading of up to 50% of the total film weight.

The peanut allergen solution is concentrated from 26.9 mg/mL up to 163.2 mg/mL of total protein content. The film weighs 89.3 mg contains 45.1 mg of total peanut protein and 2.4 mg of Ara h2.

TABLE 1

H1 Formulation:

| Film Component: | Component Mass (mg/strip) | % w/w of Dried Film: |
|---|---|---|
| Methocel E15 | 23.3 | 26.1 |
| Berry Flavoring | 2.9 | 3.3 |
| Glycerol | 1.2 | 1.3 |
| Total Peanut mass | 62.0 | 69.4 |
| Ara h2 mass | 2.4 | 2.7 |
| Peanut Protein mass | 45.1 | 50.5 |
| Total Film-Strip | 89.3 | 100.0 |

The films were prepared according to the following steps. The allergen solution was prepared by suspending the peanut extract powder at 20% w/v in deionized water, then incubating the suspension at 37° C. for 30 minutes, then centrifuging the suspension at 3,000×g for 15 minutes, and collecting the supernatant.

The allergen solution was then concentrated by flowing the solution in a loop through a Spectrum MidiKros tangential flow filtration unit with a 3 kD cutoff. The solution was pumped through via a peristaltic pump, with the proteins and larger molecules retained within the loop, and the filtrate discarded. Allergen solution was continuously added to the loop until the desired concentration is reached.

Methocel E15, glycerol, and flavoring are mixed with the concentrated allergen solution according to the quantities listed above, with vortexing and ultrasonic vibration used to mix the solution until it is uniform and bubble-free. The mixture solution is cast onto a flat surface or tray made of Teflon. The film solution is dried overnight at room temperature. The dried filmstrips are removed from the tray and are cut to strips of dosing size, 1 cm×2 cm×200 µm each. Following this step, the protein content is determined using bicinchoninic acid assay from Thermo Scientific. The specific allergen Ara h2 content in the prepared film is determined by enzyme-linked immunosorbent assay from Indoor Biotechnologies.

Example 5

Exemplary Drug Substance Used for Clinical Trial

TABLE 2

The following reagents and components were used in the formulation of the FDA phase 1 trial.

| Item | Vendor: Grade | Batch Quantity | Percentage in film strip |
|---|---|---|---|
| Defatted peanut extract | Greer: RMF-171P | 20 gm | 14.8% |
| Hypromellose 2910 USP grade: (Hydroxypropyl methylcellulose) | Dow Chemical Co.: Methocel E15 Premium LV | 100 gm | 74.0% |
| Glycerin NF grade | Spectrum Chemical and Laboratory Prod.: G1016-1LT | 2 mL | 1.5% |
| Sucralose NF grade | Spectrum Chemical and Laboratory Prod.: S1416 | 10 gm | 7.4% |
| Chocolate Flavoring | Abelei Flavors 131a62 | 3 mL | 0.2% |
| Sterile Water for Irrigation NF grade | Baxter International Corp. | Not applicable: used during manufacturing | N/A |

Note the batch size and concentration of peanut extract are typical values, to get minor differences in batch sizes and strengths of Ara h2 this basic formulation is scaled proportionally. The peanut extract is diluted with sterile water before adding to the final blend. Thus, the strength is changed by the amount of peanut extract dilution with water.

In accordance with some embodiments, various excipients can be used in accordance with of the present invention. The following Table 3 lists exemplary excipients used in a formulation for the clinical trials.

TABLE 3

List of Drug Product Components and their function.

| Component | Function | Testing |
|---|---|---|
| Hypromellose 2910 USP grade: (Hydroxypropyl methylcellulose) | Film forming polymer | USP monograph ID test and CoA |
| Glycerin NF grade | Polymer film plasticizer | NF monograph ID test and CoA |
| Sucralose NF grade | Sweetening agent | NF monograph ID test and CoA |

TABLE 3-continued

List of Drug Product Components and their function.

| Component | Function | Testing |
|---|---|---|
| Chocolate Flavoring | Flavoring agent | CoA and visual inspection |
| Sterile Water for Irrigation NF grade* | Manufacturing aid | None |

*used to facilitate film casting, but removed by drying from the final product.

The function of each component used to make the peanut immunotherapy strip is described in Table 3. Processing aids used to prepare the drug product, but which are removed during or following the subsequent process are indicated with an asterisk. In addition, all components that are in the USP or NF are identified using the specified compendial test, for the other compendial tests the manufacture's Certificate of Analysis will be used.

Example 4

Manufacturing Methods for an Embodiment of the Present Invention

Figure 2:
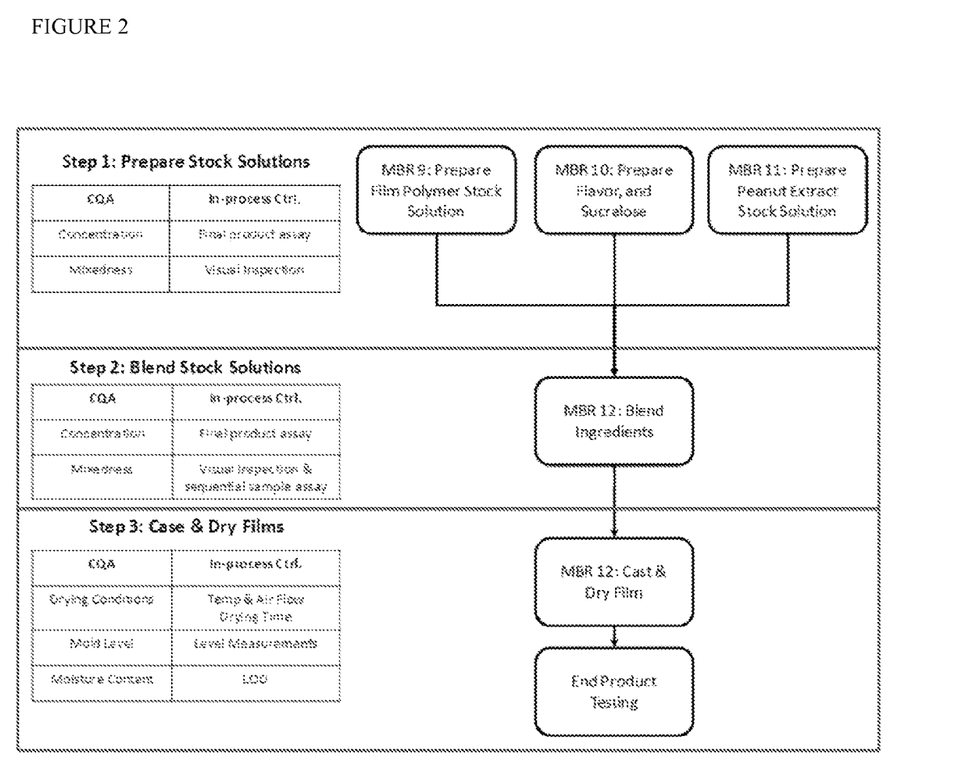
FIG. 2 is a schematic diagram depicting the manufacturing process of at least one embodiment of the present invention. The diagram shows the process controls. The following abbreviations apply: CQA=Critical Quality Attribute, reference to MBR=Master Batch Record section, Ctr.=Control.

The process flow diagram for the manufacturing of a peanut immunotherapy film strip of the present invention is shown in FIG. 2. The film strips were made by a solvent casting process in which the formulation was poured into a series of disposable Petri dish molds. Once filled with the formulation the Petri dishes were placed in a leveled convection oven until dry. The solvent casting procedures involve the three steps shown in FIG. 2.

Ara h2 concentrations were assayed using Indoor Biotechnologies Rabbit anti-Ara h 2 (PA-AH2) ELISA assay. Assays were performed at Indoor Biotechnologies. The product assay limits were 80-120% of the labeled amount. For the film strips #1 and #2 the protein content was below the limits of detection of this assay. These films were assayed to ensure that the content was below the assay limit (approximately 0.008 mcg Ara H2).

Example 5

Protocol for Clinical Study and Evaluation

An open label, non-blinded phase I trial was conducted to evaluate the safety and efficacy of a new formulation of peanut protein immunotherapy for treatment of peanut allergy in peanut allergic adults is provided. Initially 5 non-peanut allergic subjects at Johns Hopkins Hospital were enrolled for an accelerated pilot safety study. These subjects had an initial screening visit that included informed consent, medical exam and history, and if they were eligible for the study, an initial dose escalation. They continued home daily dosing with the study product and then will return approximately one week later for further dose escalation. They continued home daily dosing for an additional three weeks. At the completion of the study they had a medical examination and daily home diaries will be returned and reviewed. There were no side effects reported except for dry mouth. Permission was given by FDA to proceed with the phase I/II study of peanut allergic subjects.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A pharmaceutical composition suitable for use in the treatment of an allergic response in a subject consisting of:
    a) about 74% w/w of a primary film forming agent, wherein the agent comprises a sufficient amount of hydroxypropyl methyl cellulose; or polyethylene glycol, wherein the film forming agent is also a mucoadhesive polymer;
    b) about 1.5% w/w of a biodegradeable plasticizer is glycerols,
    c) about 14.8% w/w of at least one allergen extract comprising peanut extract,
    d) about 0.2% w/w of a flavoring agent, wherein the flavoring agent is also the coloring agent; and
    e) about 7.4% w/w of a sweetening agent.

2. The pharmaceutical composition of claim 1, wherein the composition is prepared as a thin film with a thickness of between about 50 to about 500 pm.

3. The pharmaceutical composition of claim 2, wherein the thin film is cut into strips having dimension of about 1×2 cm.

4. A method for treatment of an allergic response to an antigen in a subject comprising administering to the subject a sufficient amount of at least one pharmaceutical composition consisting of a sufficient amount of hydroxypropyl methyl cellulose; or polyethylene glycol, wherein the film forming agent is also a mucoadhesive polymer;
    b) about 1.5% w/w of a biodegradeable plasticizer is glycerols, c) about 14.8% w/w of at least one allergen extract comprising peanut extract,
d) about 0.2% w/w of a flavoring agent, wherein the flavoring agent is also the coloring agent; and
e) about 7.4% w/w of a sweetening agent.

5. The method of claim 4, wherein the route of administration is buccal or sublingual.

6. The method of claim 5, wherein the route of administration is sublingual.

7. A kit comprising the pharmaceutical composition of claim 1, in an airtight container and instructions for use.

\* \* \* \* \*